United States Patent
Bachmann et al.

[11] Patent Number: 5,954,729
[45] Date of Patent: *Sep. 21, 1999

[54] TRANSLUMINAL IMPLANTATION DEVICE

[75] Inventors: Michel Bachmann, Romanel; Robert B. Nissels, Corbeyrier, both of Switzerland

[73] Assignee: Schneider (USA) Inc., Plymouth, Minn.

[ * ] Notice: This patent is subject to a terminal disclaimer.

[21] Appl. No.: 08/957,179

[22] Filed: Oct. 24, 1997

Related U.S. Application Data

[62] Division of application No. 08/723,939, Sep. 26, 1996, Pat. No. 5,759,186, which is a division of application No. 08/207,324, Mar. 7, 1994, Pat. No. 5,591,172, which is a continuation-in-part of application No. 07/891,887, Jun. 1, 1992, abandoned.

[30] Foreign Application Priority Data

Jun. 14, 1991 [SE] Sweden ................................. 9101841

[51] Int. Cl.[6] .................................................. A61B 17/00
[52] U.S. Cl. ........................................ 606/108; 606/198
[58] Field of Search .................... 606/108, 195, 606/198, 191

[56] References Cited

U.S. PATENT DOCUMENTS

| | | | |
|---|---|---|---|
| 4,665,918 | 5/1987 | Garza et al. | 606/198 |
| 4,732,152 | 3/1988 | Wallsten et al. | 623/12 |
| 4,954,126 | 9/1990 | Wallsten | 606/198 |
| 4,990,151 | 2/1991 | Wallsten | 606/108 |
| 5,026,377 | 6/1991 | Burton et al. | 606/108 |
| 5,160,341 | 11/1992 | Brenneman et al. | 606/198 |
| 5,693,083 | 12/1997 | Baker et al. | 623/1 |

*Primary Examiner*—Richard J. Apley
*Assistant Examiner*—Justine R. Yu
*Attorney, Agent, or Firm*—Vidas, Arrett & Steinkraus, P.A

[57] ABSTRACT

A device for transluminal implantation of a substantially tubular, radially expansible stent. The device includes a central tube surrounded by an outer tube axially displaceable relative to the central tube, with the radial dimensions of the tubes being such as to form an annular space therebetween capable of accommodating the stent in an unexpanded state. The outer tube is axially displaceable relative to the central tube. In one embodiment of the device, the central tube, at a distal end thereof, is provided with a section of reduced diameter at the proximal end of which there is an undercut groove forming a circumferential flange within which a proximal end of the stent rests until release of the stent by rearward displacement of the outer tube. In a modification of the device, the central tube, at its distal end, includes a sleeve slidably positioned therearound for capturing at least a proximal portion of the stent restraining the proximal portion against movement until stent deployment.

12 Claims, 7 Drawing Sheets

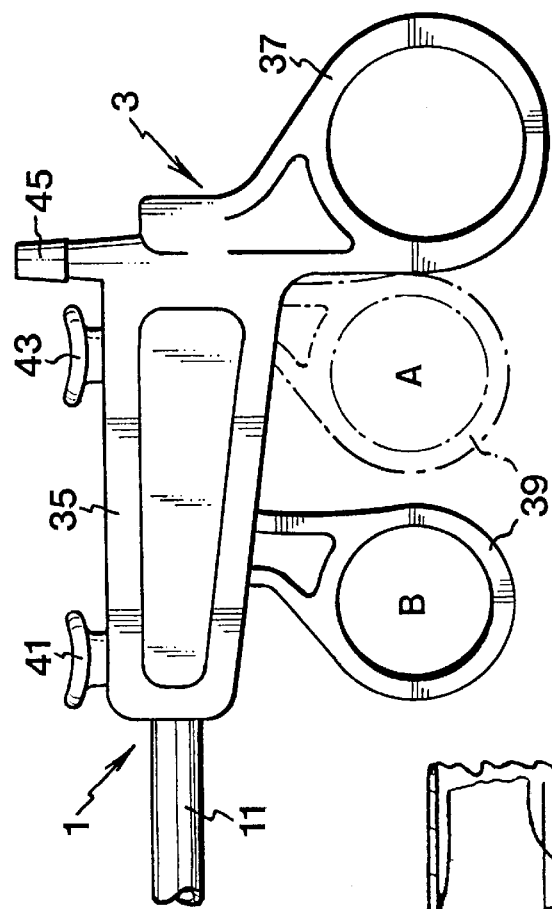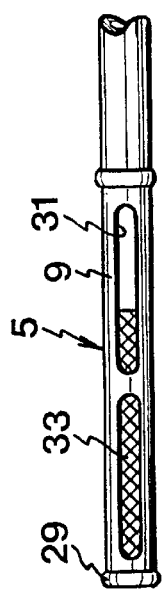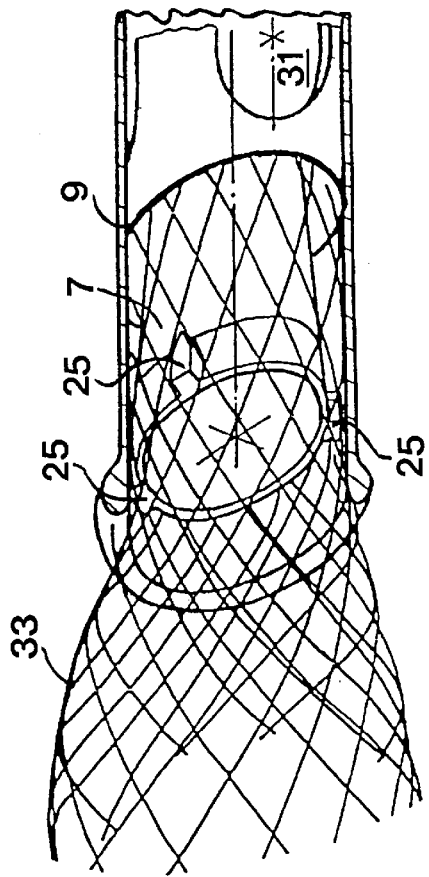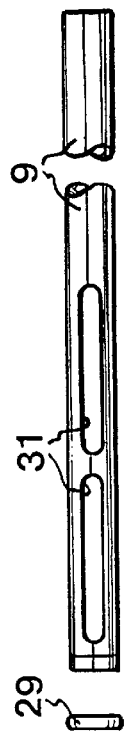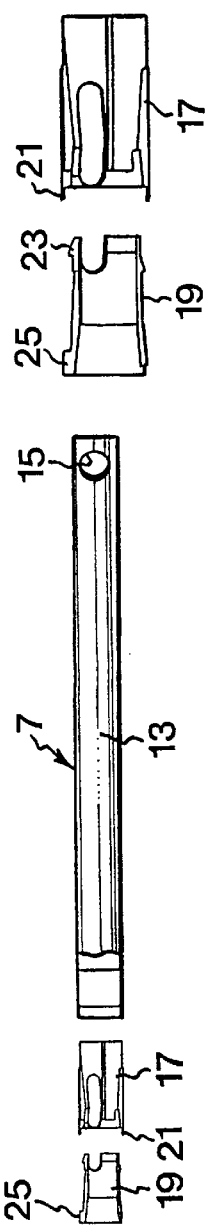

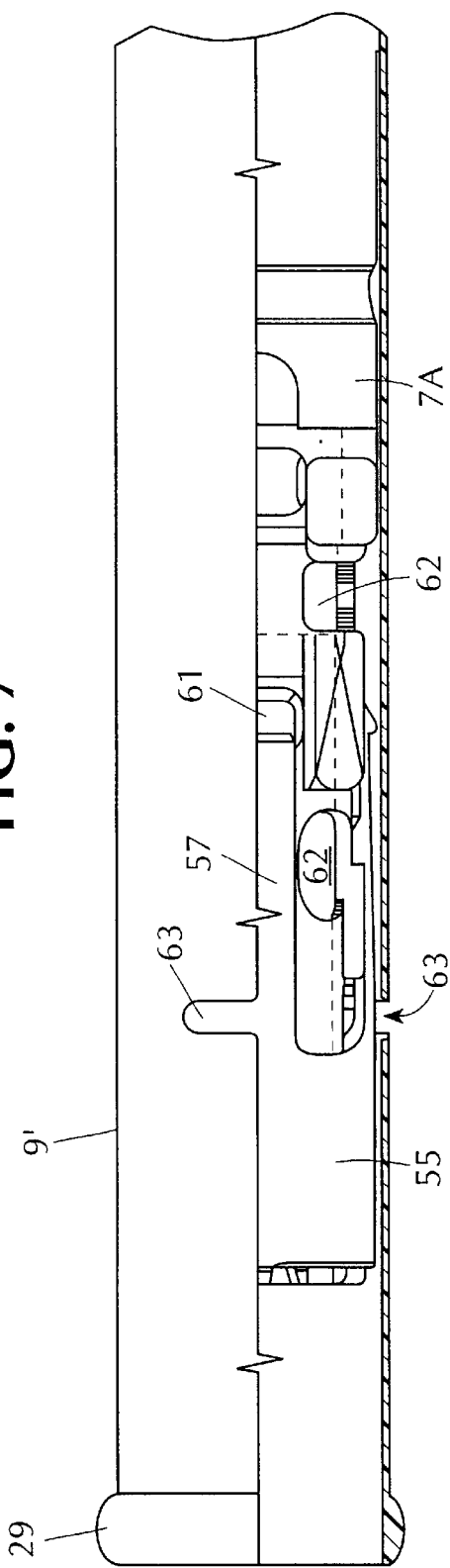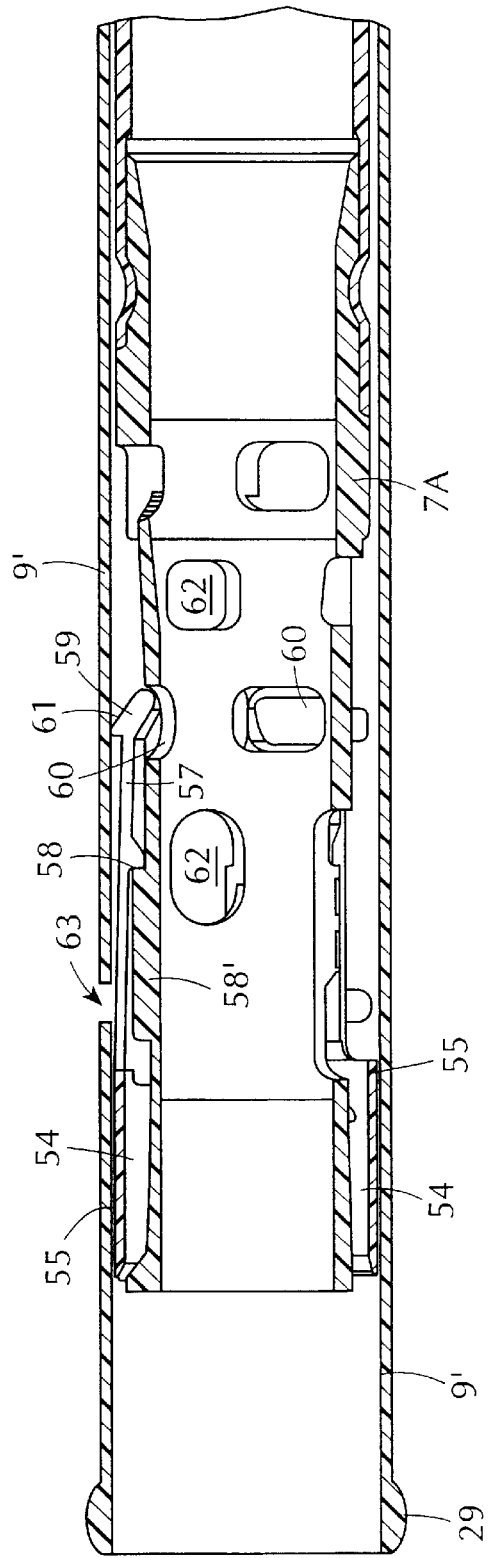

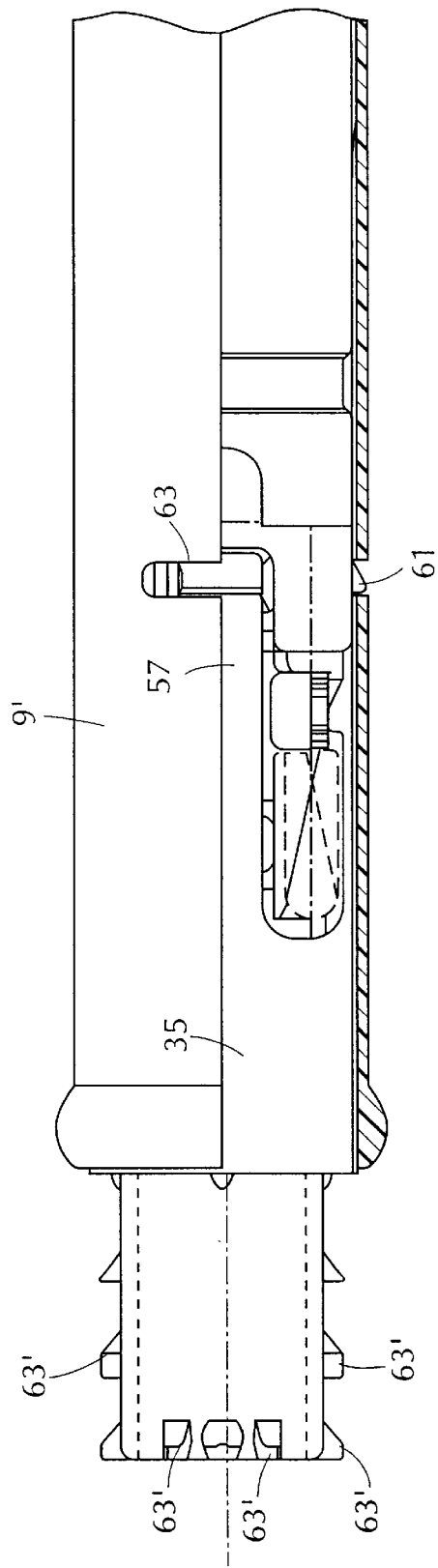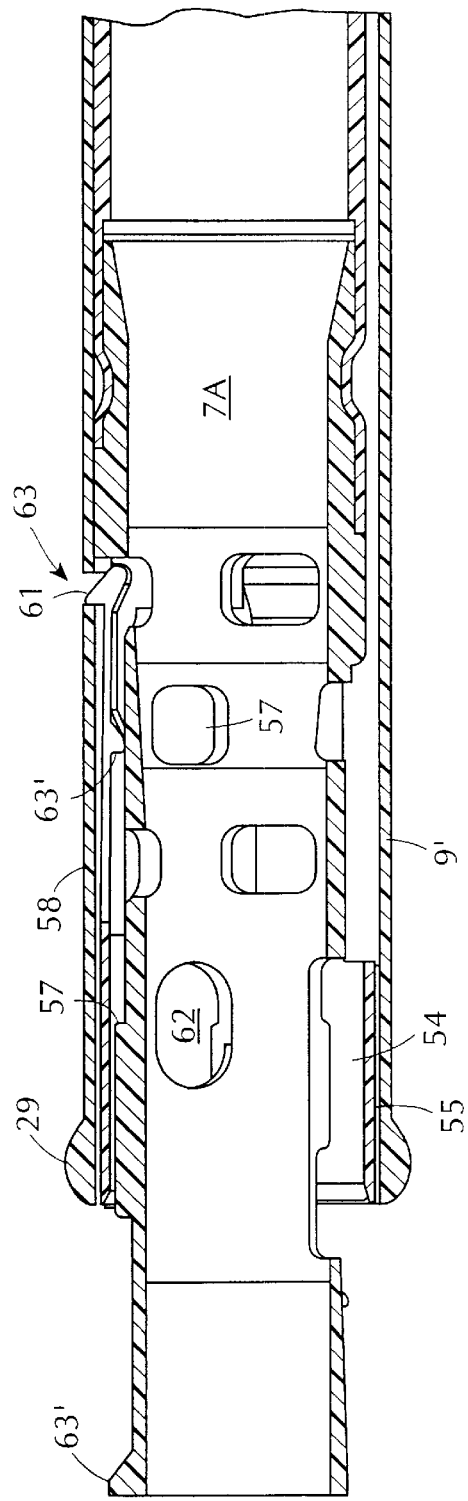

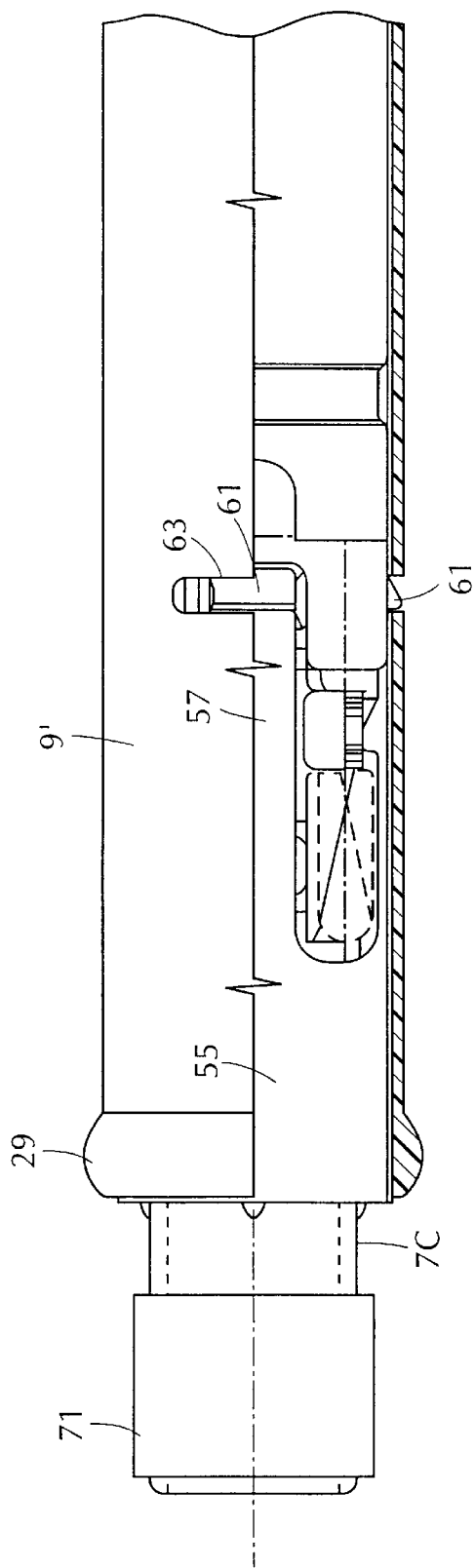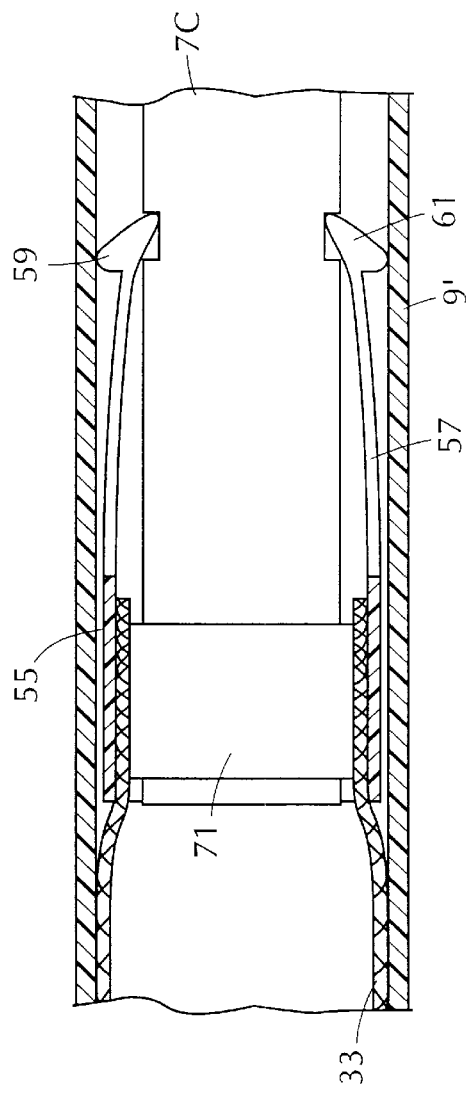

TRANSLUMINAL IMPLANTATION DEVICE

This application is a division of application Ser. No. 08/723,939, filed Sep. 26, 1996, now U.S. Pat. No. 5,759,186, which is a division of application Ser. No. 08/207,324, filed Mar. 7, 1994, now U.S. Pat. No. 5,591,172 which is a continuation-in-part of application Ser. No. 07/891,887, filed on Jun. 1, 1992 now abandoned.

BACKGROUND OF THE INVENTION

The present invention relates to a device for transluminal implantation of a substantially tubular, radially expansible stent.

Devices for transluminal implantation of expanding stents or prostheses are previously known. Thus, U.S. Pat. No. 4,732,152 describes a device enabling transluminal implantation of self-expanding stents. The device described in said U.S. patent shows excellent performance in regard to enabling implantation of prostheses or stents in for example blood vessels or other ducts in living animal bodies. Said U.S. patent exemplifies operation with prostheses or stents of the type disclosed in U.S. Pat. No. 4,655,771. This particular type of prostheses for use in transluminal implantation comprises a flexible tubular body composed of a braided arrangement of flexible thread elements involving free ends at the axial extremes of the prostheses. Although the present invention is not limited to transluminal implantation of the type of prostheses or stents disclosed in U.S. Pat. No. 4,655,771, the present invention will be illustrated with special reference to such stents. In practical operation it has been found that handling such stents in connection with transluminal implantation thereof involves practical problems related to particularly the rear or proximal end of the stent and its association with the implantation device. Thus, it has been found that radial observation openings may be needed in the concentric tubes involved in connection with the implantation procedure in order to properly locate the stent before its release at the site of implantation. Such observation openings result in practical complications due to interaction with the rear end of the stent which may result in operational problems and even failure to provide for proper implantation.

SUMMARY OF THE INVENTION

The present invention has for its main object to solve the problems associated with implantation devices capable of providing for insertion and release of prostheses or stents of different types, for example of the type disclosed in U.S. Pat. No. 4,655,771.

Another object of the invention is to provide for a device that provides for safety operation in the implantation procedure and enabling proper positioning of expanding stents in connection with their implantation.

For these and other objects which will be better understood by the following disclosure, the invention provides a device for transluminal implantation of a substantially tubular, radially expansible stent, the device comprising a central tube or rod surrounded by an outer tube which is axially displaceable relative to the central tube or rod, the radial dimensions of the tubes or tube and rod being such as to form an annular space therebetween capable of accommodating the stent in an unexpanded state. The device further comprises means for axial displacement of the outer tube relative to the central tube or rod. In one aspect of the device of the present invention, the central tube or rod, at the distal or front end thereof, is provided with a section of reduced diameter at the proximal or rear end of which there is an undercut groove forming a circumferential flange within which the proximal or rear end of the stent rests until release of the stent by rearward displacement of the outer tube. In a modification of the invention, the central tube at its distal end includes a sleeve slidably positioned therearound for capturing a proximal portion of the stent and restraining the proximal stent portion against movement. Preferably, the proximal portion of the stent is positioned between the sleeve and the central tube. The proximal portion of the stent remains stationary until release thereof by rearward displacement of the sleeve and the outer tube whereafter the stent becomes fully deployed.

In the instant disclosure the expressions "distal" and "proximal" refer to the stent end and the handle end, respectively, of the associated construction detail or element. The distal end of the stent will be that portion located farthest from the handle end whereas the proximal end of the stent will be that portion located closest to the handle end.

In one embodiment of the device of the invention, the central tube or rod is provided at the distal end thereof with at least two radially extending members engaging the stent from the inside to facilitate its release. The number of members is preferably at least three, and the members are preferably substantially evenly circumferentially distributed around the distal end. The members might be conical teeth or truncated conical teeth.

Preferably, in the sleeve modification, the sleeve includes a releasable latching feature for maintaining the sleeve in a first position on the central tube. One or more claw members of the sleeve coact with the outer tube to bias the claw member into engagement with a recess or opening in the central tube. In a preferred configuration, the claw members number at least three substantially evenly circumferentially distributed around the sleeve. The central tube might include a guide track to allow for linear axial movement of the claw member and prevent sleeve rotation. The outer tube includes a feature for releasing the sleeve claw member and engaging the sleeve so that the sleeve might be moved to a second position wherein the proximal portion of the stent is released and the stent fully deployed. In another modification of the stent capturing aspect at the proximal end of the stent, both the sleeve and the central tube are complementarily conically tapered for capturing and restraining the stent between abutting tapered surfaces. In yet another modification, the central tube further includes a cuff member wherein the proximal portion of the stent is captured between the cuff and the sleeve.

It is preferred that the outer tube is provided with radial openings in the area thereof comprising the location of the stent so as to enable inspection of the position of the stent during its implantation. It is additionally preferred that the central tube includes one or more radial openings for monitoring the positioning of the stent during stent implantation. As an alternative said outer tube can be made of a transparent material to enable such inspection.

In the device according to the invention, it is preferred that the axial displacement means enabling axial relative movement between the central tube or rod and the outer tube includes safety catches defining the extreme axial positions of the outer tube. The purpose of the safety catches is to avoid untimely deployment of the stent during the insertion procedure or complete release before the correct position has been reached.

In a particularly preferred embodiment of the device according to the invention, the central tube is capable of accommodating viewing means, such as an endoscope or telescope, positioned inside the tube and axially displaceable therein.

The axial displacement means may be provided with a fluid inlet for flushing or for the injection of contrast media. Thus, such fluid inlet can be used for introducing flushing liquid to remove contaminants from the interior of the instrument or for introducing a contrast medium to enable X-ray inspection to facilitate positioning of the instrument during the implantation procedure.

The invention also covers an apparatus for the implantation of an expansible stent comprising an implantation device as outlined above in combination with such stent positioned in the annular space in a contracted state. Positioned in this manner the proximal or rear end of the stent is located either within the undercut groove or between the sleeve and the central tube and is thus protected from damages or dislocation of its constructional elements. It is preferred that the stent is of the self-expanding type and especially preferred are stents of the type described in U.S. Pat. No. 4,655,771, the contents of which are incorporated herein by reference. In accordance with the disclosure of this U.S. patent, the stent is in brief constituted by a flexible tubular body which has a diameter that is variable by axial movement of the ends of the body relative to each other and which is composed of several individual rigid but flexible thread elements each of which extends in helix configuration with the center line of the body as a common axis, a number of elements having the same direction of winding but being axially displaced relative to each other crossing a number of elements also axially displaced relative to each other but having the opposite direction of winding.

BRIEF DESCRIPTION OF THE DRAWINGS

The present invention will now be described by a non-limiting example with reference to the appended drawings, wherein:

FIG. 1 is a diagrammatic side view of a preferred embodiment of the device of the invention;

FIG. 2 shows a detail of the device of FIG. 1;

FIG. 3 shows another detail in an exploded view of the instrument of FIG. 1;

FIG. 4 is a detail view in enlargement of the proximal end of the detail of FIG. 3.

FIG. 5 is an enlarged detail view of the proximal end of the instrument including a stent under release.

FIGS. 7–16 illustrate modifications to the present invention, wherein:

FIG. 7 shows an enlarged, schematic, partial, cutaway view of a modification of the distal end of the device of FIG. 1;

FIG. 8 depicts a sectional view of the illustration of FIG. 7;

FIG. 9 is a view like that of FIG. 7 but with the outer tube moved rearwardly to a second position;

FIG. 10 is a sectional view of the illustration of FIG. 9;

FIG. 11 is also a view like that of FIG. 7 but with the outer tube moved further rearwardly to a third position;

FIG. 12 is a sectional view of the illustration of FIG. 11;

FIG. 13 depicts a view like that of FIG. 10 but with a modified sleeve and a modified central tube at the distal ends;

FIG. 14 is a view like that of FIG. 12 but with the modification depicted in FIG. 13;

FIG. 15 is a view similar to that of FIG. 11 but further including a cuff member at the distal end of the central tube; and FIG. 16 schematically depicts a partial sectional view of the illustration of FIG. 15 but further includes a stent prior to stent deployment.

DETAILED DESCRIPTION OF THE PREFERRED EMBODIMENTS

Figure 6:
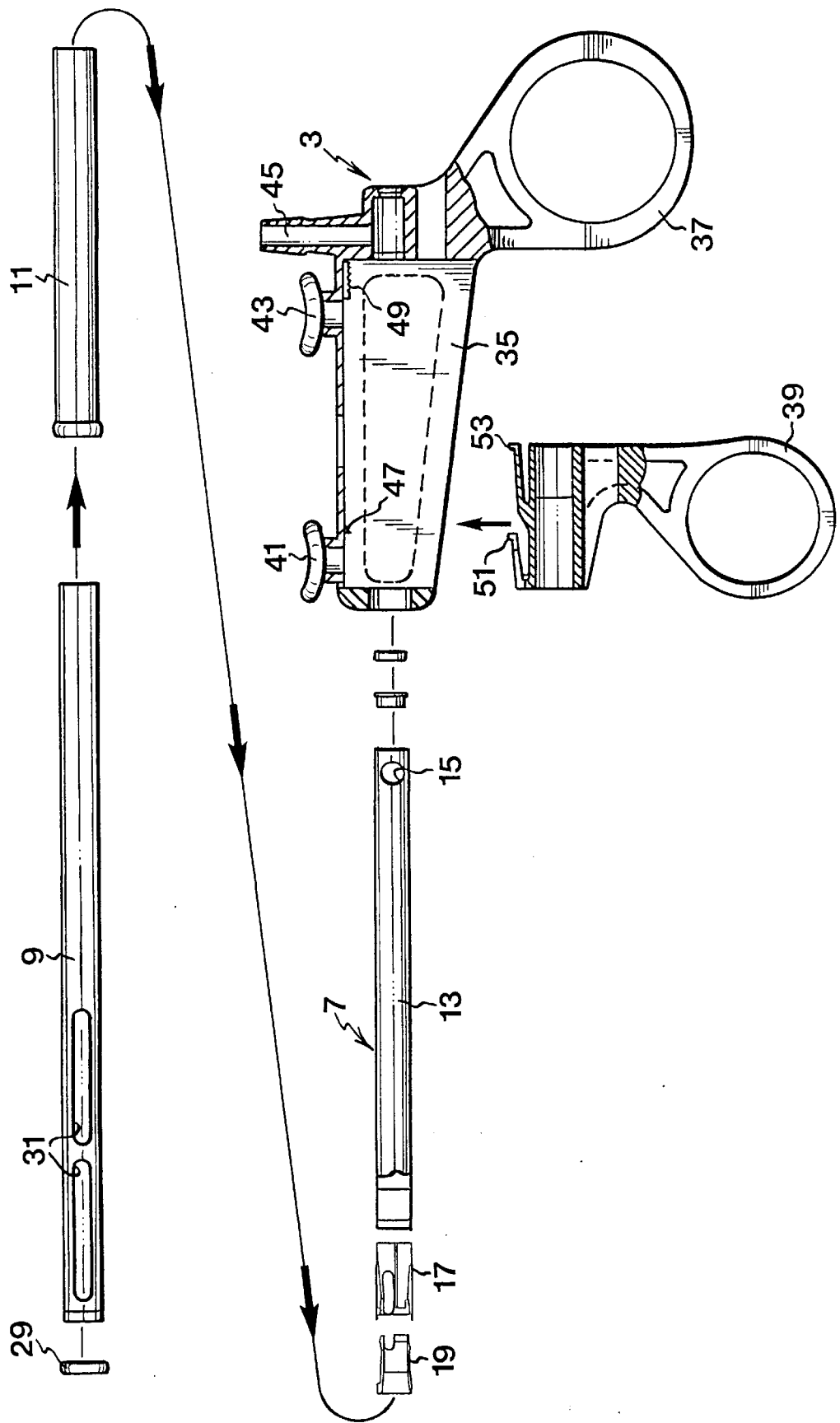
FIG. 6 is an exploded side view of the device of FIG. 1 showing more in detail its different parts.

The device or delivery system, shown in FIG. 1 is generally designated 1 and the device comprises in principal at the proximal end thereof operating means generally designated 3 and at the distal end thereof implantation means generally designated 5. The implantation means 5 is in the form of elongated catheter means which comprises a central (i.e. through the lumen of the central tube 7) tube generally designated 7 surrounded by an outer tube or pull back shaft 9, said outer tube 9 at the rear or proximal end thereof being surrounded by a further outer tube or stabilizing exterior tube 11 attached to operating means 3.

Central tube 7 is shown more in detail by exploded views in FIGS. 3 and 4. Central tube 7 contains a main part 13 provided with one opening 15 for a purpose to be explained below. Furthermore, it contains a middle part 17, the rear end of which can be inserted into and attached to the main part 13. Finally, central tube 7 includes a front end part 19 having a rear end 23 of reduced diameter and having a tapered shape for insertion into and fixation to the front end of the middle part 17. The front end part 19 of the central tube 7 is provided at its distal end with hooks or extensions 25 for a purpose to be further explained below. In the embodiment shown the number of hooks 25 is three as is evident from FIG. 5. The hooks are evenly distributed around the periphery of the front end part 19.

The middle part 17 of central tube 7 is at its distal end provided with a forwardly directed circumferential flange 21 which when the front end part 19 is inserted into the front end of middle part 17 forms an undercut groove or recess that can accommodate the rear end of stent 33 in the position shown in FIG. 1, i.e. with the stent (i.e. medical device) in a contracted state.

The outer tube 9 is shown by an exploded view in FIG. 2. At the distal end thereof it is provided with a rounded collar 29 to facilitate insertion during implantation. Furthermore, it is provided with axially extending elongate radial openings 31 for a purpose that will be explained below. At the rear end thereof outer tube 9 is surrounded by a stabilizing exterior tube or stiffening shaft 11 which is attached to the operating means 3, whereas the outer tube 9 is axially displaceable within the exterior tube 11. Preferably, stabilizing tube 11 maintains a fixed position.

In regard to the design of the rear end operating means 3, generally designated 3, reference is now made to FIGS. 1 and 6. FIG. 1 is an assembly drawing of the device, whereas FIG. 6 shows an exploded view of the device. Operating means 3 comprises a main body 35 and integral therewith a rear loop handle 37. Operating means 3 further includes a moveable second loop handle 39 which is displaceable between extreme positions within the main body 35 indicated by dashed lines and full lines in FIG. 1 illustrating retracted position and forward position, respectively. The outer tube 9 is permanently attached to the front end of the moveable second loop handle 39 and is thus axially moveable forward and backward between the extreme positions by moving loop handle 39. Operating means 3 includes a front safety catch release member 41 and a rear safety catch release member 43 corresponding to the two extreme positions indicated in FIG. 1 by positions B (full lines) and A (dashed lines), respectively. Release members 41, 43 cooperate with spring elements 51 and 53, respectively, provided on the upper side of the second loop handle 39 as shown in FIG. 6. These springing elements 51, 53 cooperate with safety catches 47, 49 provided on the inside of main body 35. By pressing release members 41, 43 springing elements 51 and 53, respectively, can be released from their engagement with the respective safety catches 47, 49 so that the second loop handle 39 can be axially displaced together with the associated outer tube 9.

Finally, the main body 35 at the rear end thereof is provided with a fluid inlet 45 allowing introduction of a fluid into the instrument, such as a liquid for flushing or a contrast medium for X-ray inspection. Such fluid entering fluid inlet 45 passes through opening 15 into and through the central tube 7 or inner shaft or for the removal of contaminants at the location of stent 33 or for providing contrast for X-ray inspection.

As noted above stabilizing tube 11 maintains a fixed position with respect to operating means 3, in contrast to tube 9 being axially displaceable within tube 11. Because central tube 7 is mounted to operating means 3 in such a manner that its opening 15 is located at inlet 45 of operating means 3, tube 7 is also maintained in a fixed position with respect to operating means 3. By having both tube 7 and tube 11 fixedly or non-movably mounted to the same operating means 3 at their proximal ends (see FIGS. 1 and 6), axial movement is prevented of tube 7 with respect to tube 11. Thus, the connection of tube 11 to tube 7 (by means of their common connection to operating means 3) prevents axial movement of tube 7 with respect to tube 11, thereby preventing the distal end of tube 7 from being urged forward during delivery of stent 33.

Turning now to FIGS. 7–16, we will now describe modifications to the present invention. Firstly, in FIGS. 7–12 there is depicted a modified portion of device 1 for holding stent 33. While stent 33 is not actually depicted in these views, it will readily be appreciated how the stent is captured and positioned in the device in a stent capture zone 54 prior to stent deployment. (For example, FIG. 16 schematically shows stent 33 in position before release from another modified version of device 1.) Here the stent holding feature is illustrated as a two piece construction, namely a sleeve 55 including a claw-like member 57 coacting with outer tube 9' and central tube 7A to lock or hold the proximal end of the stent in place. In one preferred modification, sleeve 55 has three claws 57 evenly distributed around the sleeve. Each claw 57 is equipped with an internal clip 59 and an external clip 61. Each claw 57 may have an additional stop clip 58 which contacts a raised portion 58' on central tube 7A to further limit the movement of sleeve 55 and to keep the sleeve from coming loose. Stent 33 is immobilized on central tube 7A by projecting members or teeth 63' (see FIG. 11) that catch or engage the mesh of the stent from the inside. The size and arrangement of the teeth on the central tube are suitable for accepting stents with widely varying parameters, for example, thread diameter and thread crossing angles. The teeth are conical, and preferably truncated, to permit release of the stent even in cases of misalignment of the outer tube with the area to be treated or in the event of a curved treatment zone. The diameter of sleeve 55 is slightly larger than the diameter of central tube 7A at teeth 63' so that the sleeve can slide without dislodging the stent.

The sleeve is long enough to conform to the stent in such a way as to minimize stent movement as tube 9' is retracted. Additionally, the sleeve is long enough to prevent the proximal end of the stent from coming into contact with the inner wall of outer tube 9'.

Figure 9:
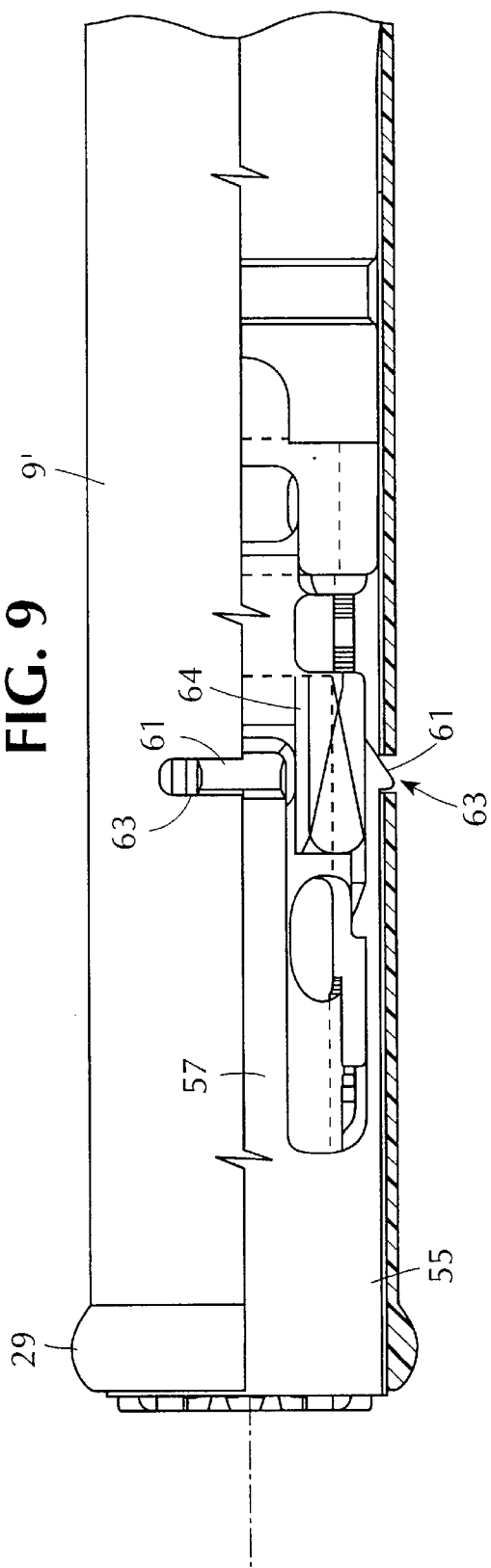
Figure 10:
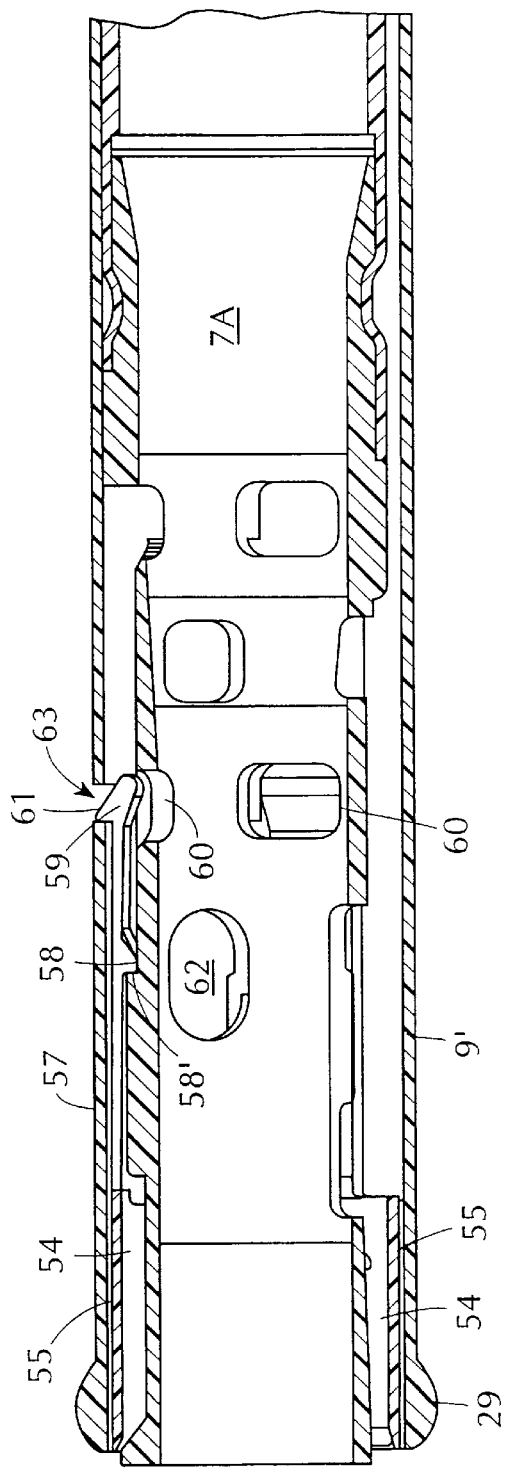

Internal clip 59 of claw 57 serves to ensure a two-position indexing function. Sleeve 55 remains in the distal position (FIGS. 7 and 8) as long as the guide-implant or outer tube 9' has not been drawn back beyond the sleeve engaging position, a position which can only be reached by activating the second safety 43. Here clip 59 is positioned in a hole or recess 60 of central tube 7A to hold sleeve 55 in place. It is outer tube 9' which biases spring-like claw 57 into this releasable latching or locking position. A number of radial openings 62 in central tube 7A permit or enable monitoring or inspection of the positioning of the proximal end of the stent during implantation and viewing of the features of the body duct or canal before and after treatment. Additionally, openings 62 allow for an increase of flow of flushing or contrast fluid. FIGS. 9' and 10 show outer tube 9' drawn back to a position where external clip 61 engages hooking zone 63 (a recess or opening) in outer tube 9'. (Central tube 7A might be provided with a track 64 for axially or linearly guiding claw 57.) In going beyond this position, the hooking zone 63 comes alongside external clip 61 located on claw 57 of sleeve 55. Further movement of the outer tube rearwardly will cause sleeve 55 to also move rearwardly and this is shown in FIGS. 11 and 12. As outer tube 9' moves rearwardly, at hooking zone 63 the elastic effect of claw 57 causes the claw internal clip 59 to disengage from recess 60 and external clip 61 to engage outer tube 9' at zone 63. The sleeve 55 is then drawn back together with outer tube 9' until the proximal end of the stent is no longer covered by the sleeve whereupon the stent is released from device 1 for deployment. The stent, due to self-expandable and form-memory effect, disengages from the central tube and expands up against the walls of a canal or body duct to be treated. The device 1 can then be withdrawn from a patient.

Figure 13:
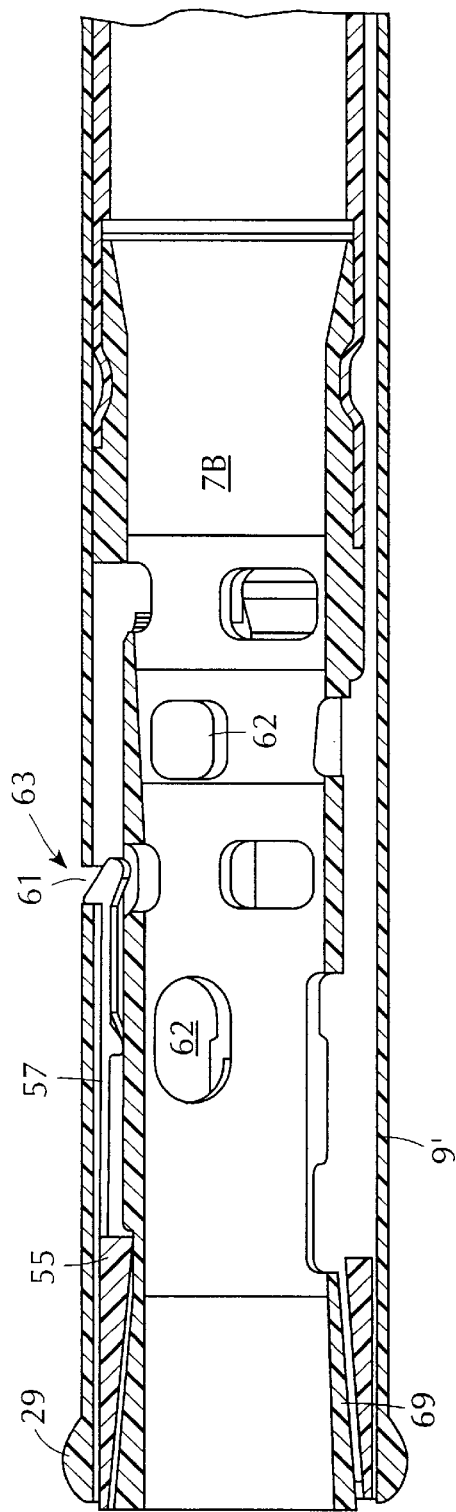
Figure 14:
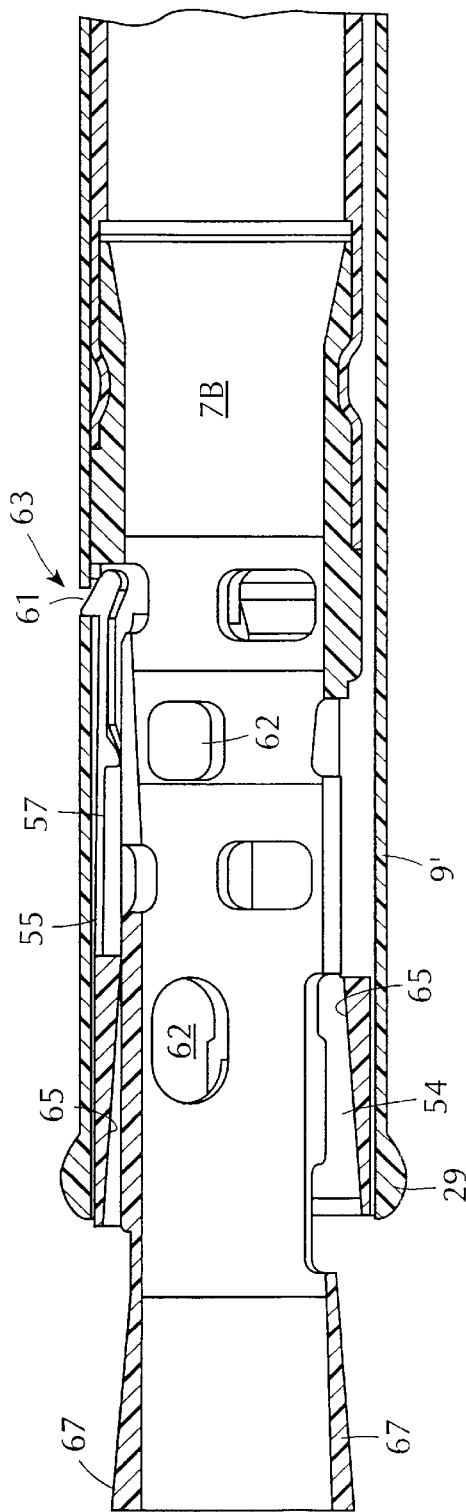

FIGS. 13 and 14 show yet another modification of the proximal stent capturing feature of the invention. Here the distal end of sleeve 55 is conically tapered as shown at 65 and the distal end of central tube 7B is conically tapered as shown at 67. The sleeve and tube are complementarily conically tapered. Although not specifically shown, it should be appreciated that the proximal portion or end of stent 33 would be captured in a zone 69 (FIG. 13) along which the conical portions 65, 67 of the central tube and sleeve adjoin or abut.

Lastly, FIGS. 15 and 16 show yet an additional modification of the proximal stent capturing feature of the invention. Here at the distal end of central tube 7C cuff 71 replaces teeth 63' and surrounds the central tube and, as shown in FIG. 16, the proximal end portion of stent 33 is positioned between cuff 71 and sleeve 55. The cuff grips the stent against the inside of the sleeve. All of the other features of the device are as set forth in FIGS. 7–12.

The function of the implantation device 1 will now be described briefly as follows:

Assuming introduction of a stent into a patient, a stent 33 of suitable dimensions is introduced into the instrument by inserting the proximal end thereof into the annular groove formed by flange 21 of the middle part 17 of central tube 7. Alternatively, the proximal end of the stent is captured between a sleeve 55 and central tube 7. The procedure is performed with the second loop handle 39 in A-position as shown by dashed lines in FIG. 1. By moving the second loop handle 39 forwardly to position B, outer tube 9 is moved into the position shown in FIG. 1. At this moment the safety catch involving members 47 and 51 has been activated keeping the second loop handle 39 securely in position B. Bringing stent 33 into the outer tube 9 by forward movement of the second loop handle 39 is facilitated by the engagement of hooks 25 with stent 33 from the inside thereof as seen in FIG. 5.

After introducing the distal end of device 1 into the patient at the desired site or location thereof, as checked by for example an endoscope or telescope, the forward safety catch release member 41 is activated by downward movement thereof thereby releasing the safety catch 47, 51 and the second loop handle 39 with associated outer tube 9 can now be moved backward to release the stent 33 as shown in FIG. 5. During this backward movement of said handle 39, the safety catch 49, 53 arrests the movement before full release of the stent. This is a safety measure and full release is obtained by pressing release member 43. When the second loop handle 39 has reached position A in FIG. 1, the stent 33 will be fully released at the desired location and the device 1 can be retracted leaving the stent 33 inside the urethra.

In the application illustrated above, implantation means generally designated 5 can be made of a rigid material, whereas in other applications involving tortuous implantation parts, they can be made of flexible materials enabling bending to follow the contour of the implantation path.

It is to be noted that the present invention is in no way limited to the embodiments described above. Thus any suitable materials can be used for the different parts of the device and, furthermore, the invention is useful not only with regard to the type of stents described in U.S. Pat. No. 4,655,771, although the device described herein is particularly useful in handling such a stent. As previously noted such self-expanding stents, as disclosed herein, can be implanted in for example blood vessels or other ducts in living animal bodies.

We claim:

1. A delivery system for implantation of a medical device in a vessel, comprising:
    a medical device;
    an elongate catheter having proximal and distal ends for delivering the medical device to a predetermined location in a vessel of a patient, the elongate catheter being further comprised of:
        an inner shaft which carries the medical device near its distal end,
        a middle pull back shaft arranged around the inner shaft, the medical device being carried between the inner shaft and middle pull back shaft, and
        an outer stiffening shaft arranged around the middle pull back shaft, the inner and outer shafts being irremovably connected at their proximal ends to prevent axial movement of the inner shaft with respect to the outer shaft,
    whereby the medical device is delivered at the desired site by pulling on a proximal end of the middle pull back shaft, which deploys the medical device, and where the outer stiffening shaft connection to the inner shaft prevents axial movement of the inner shaft with respect to the outer stiffening shaft, thereby preventing the distal end of the inner shaft from being urged forward during delivery and therefore allowing for more accurate placement of the medical device.

2. The delivery system of claim 1 wherein the elongate catheter is flexible, and the outer stiffening shaft is concentrically arranged around the middle shaft which is concentrically arranged around the inner shaft.

3. The delivery system of claim 1 wherein the medical device has an axial length and further wherein the inner and outer shafts are connected together far enough apart to allow the middle pull back shaft to retract a distance at least as great as the axial length of the medical device to be delivered.

4. The delivery system of claim 1 wherein the inner shaft has a lumen.

5. The delivery system of claim 1 wherein the medical device is a self-expanding stent.

6. A method of delivering a medical device using the delivery system of claim 1, comprising the steps of:
    providing the delivery system of claim 1,
    moving the distal end of the elongate catheter to a delivery site, and
    delivering the medical device by pulling back on the middle pull back shaft which releases the medical device,
    whereby the outer stiffening shaft connection to the inner shaft prevents the distal end of the inner shaft from being urged forward as the middle pull back shaft is retracted, thereby allowing for more accurate placement of the medical device.

7. A delivery system for implantation of a medical device in a vessel, comprising:
    a medical device;
    an elongate catheter means having proximal and distal ends for delivering the medical device to a predetermined location in a vessel of a patient, the elongate catheter means being further comprised of:
        an inner shaft which carries the medical device near its distal end,
        a middle pull back shaft arranged around the inner shaft, the medical device being carried between the inner shaft and middle pull back shaft,
        and an outer stiffening shaft arranged around the middle pull back shaft, the inner and outer shafts being irremovably connected together at their proximal ends to prevent axial movement of the inner shaft with respect to the outer shaft during delivery of the medical device to the desired site and subsequent removal of the inner and outer shafts away from the medical device,
    whereby the medical device is delivered at the desired site by pulling on a proximal end of the middle pull back shaft, which deploys the medical device, and where the outer stiffening shaft connection to the inner shaft prevents axial movement of the inner shaft with respect to the outer stiffening shaft, thereby preventing the distal end of the inner shaft from being urged forward during delivery and therefore allowing for more accurate placement of the medical device.

8. The delivery system of claim 7 wherein the elongate catheter is flexible, and the outer shaft is concentrically arranged around the middle shaft which is concentrically around the inner shaft.

9. The delivery system of claim 7 wherein the medical device has an axial length and further wherein the inner and outer shafts are connected together far enough apart to allow the middle pull back shaft to retract a distance at least as great as the axial length of the medical device to be delivered.

10. The delivery system of claim 7 wherein the inner shaft has a lumen.

11. The delivery system of claim 7 wherein the medical device is a self-expanding stent.

12. A method of delivering a medical device using the delivery system of claim 7, comprising the steps of:

providing the delivery system of claim 7, moving the distal end of the elongate catheter to a delivery site, and delivering the medical device by pulling back on the middle pull back shaft which releases the medical device, whereby the outer stiffening shaft connection to the inner shaft prevents the distal end of the inner shaft from being urged forward as the middle pull back shaft is retracted, thereby allowing for more accurate placement of the medical device.

\* \* \* \* \*